(12) United States Patent
Brady et al.

(10) Patent No.: US 6,923,815 B2
(45) Date of Patent: Aug. 2, 2005

(54) INTRAOCULAR LENS INSERTION APPARATUS

(75) Inventors: Daniel G. Brady, San Juan Capistrano, CA (US); Harish C. Makker, Mission Viejo, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 65 days.

(21) Appl. No.: 10/145,233

(22) Filed: May 14, 2002

(65) Prior Publication Data

US 2003/0216745 A1 Nov. 20, 2003

(51) Int. Cl.$^7$ .................................................. A61F 9/00
(52) U.S. Cl. ........................ 606/107; 606/103; 623/6.12
(58) Field of Search ................................ 606/107, 103, 606/1; 623/6.12, 4.1, 6.11; 604/57, 58, 59, 64; 222/630, 631, 632

(56) References Cited

U.S. PATENT DOCUMENTS

| | | | |
|---|---|---|---|
| 4,681,102 A | | 7/1987 | Bartell |
| 4,785,810 A | | 11/1988 | Buccala et al. |
| 4,834,094 A | | 5/1989 | Patton et al. |
| 4,836,201 A | * | 6/1989 | Patton et al. ............... 606/107 |
| 4,919,130 A | | 4/1990 | Stoy et al. |
| 4,934,363 A | | 6/1990 | Smith et al. |
| 5,190,552 A | | 3/1993 | Kelman |
| 5,304,182 A | | 4/1994 | Rheinish et al. |
| 5,451,229 A | | 9/1995 | Geuder et al. |
| 5,474,562 A | | 12/1995 | Orchowski et al. |
| 5,494,484 A | * | 2/1996 | Feingold ..................... 606/107 |
| 5,496,328 A | | 3/1996 | Nakajima et al. |
| 5,499,987 A | | 3/1996 | Feingold |
| 5,535,746 A | | 7/1996 | Hoover et al. |
| 5,551,448 A | * | 9/1996 | Matula et al. ............... 128/897 |
| 5,643,276 A | | 7/1997 | Zaleski |
| 5,728,102 A | | 3/1998 | Feingold et al. |
| 5,735,858 A | * | 4/1998 | Makker et al. .............. 606/107 |
| 5,772,666 A | | 6/1998 | Feingold et al. |
| 5,776,138 A | * | 7/1998 | Vidal et al. .................. 606/107 |
| 5,860,984 A | | 1/1999 | Chambers et al. |
| 5,868,752 A | | 2/1999 | Makker et al. |
| 5,873,879 A | * | 2/1999 | Figueroa et al. ............ 606/107 |
| 6,010,510 A | * | 1/2000 | Brown et al. ................ 606/107 |
| 6,056,758 A | * | 5/2000 | Vidal et al. .................. 606/107 |

FOREIGN PATENT DOCUMENTS

| | | |
|---|---|---|
| EP | 0363213 | 4/1990 |
| JP | 49404 | 4/1993 |
| WO | 9513022 | 5/1995 |
| WO | 9521594 | 8/1995 |
| WO | 9522287 | 8/1995 |

* cited by examiner

*Primary Examiner*—Pedro Philogene
(74) *Attorney, Agent, or Firm*—Advanced Medical Optics, Inc.

(57) ABSTRACT

An intraocular lens (IOL) insertion system for implanting IOLs into the eye. The insertion system includes an insertion cartridge that receives the IOL and cooperates with a handpiece. The cartridge includes a longitudinal lumen from a loading chamber to an open distal mouth that gradually narrows in dimension so as to fold the IOL into a tube for insertion through an incision in the eye. A distal tip member of a plunger rod in the handpiece enters the loading chamber of the cartridge and urges the IOL therethrough. The distal tip member has a portion that enters the folded IOL and is trapped therein for maximum control of IOL advancement. A soft tip, such as silicone, may cover a longitudinally extending portion of the distal tip to effect the IOL trapping. The distal tip member further has a portion that engages and pushes the IOL optic. The pusher portion not only ensures positive advancement of the IOL, but also limits the extent to which the distal tip member becomes trapped inside the folded IOL, thus preventing potential damage thereto.

16 Claims, 4 Drawing Sheets

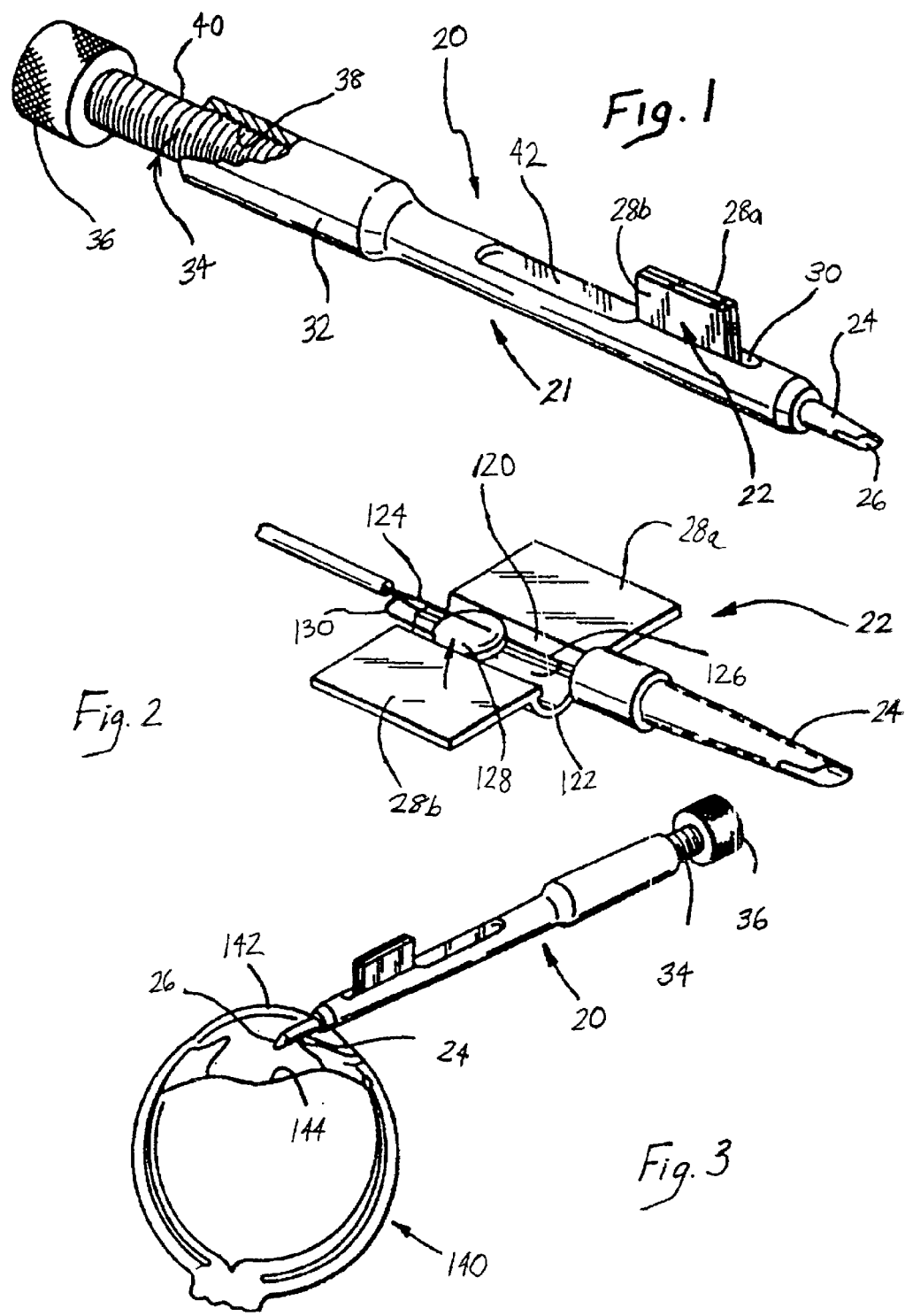

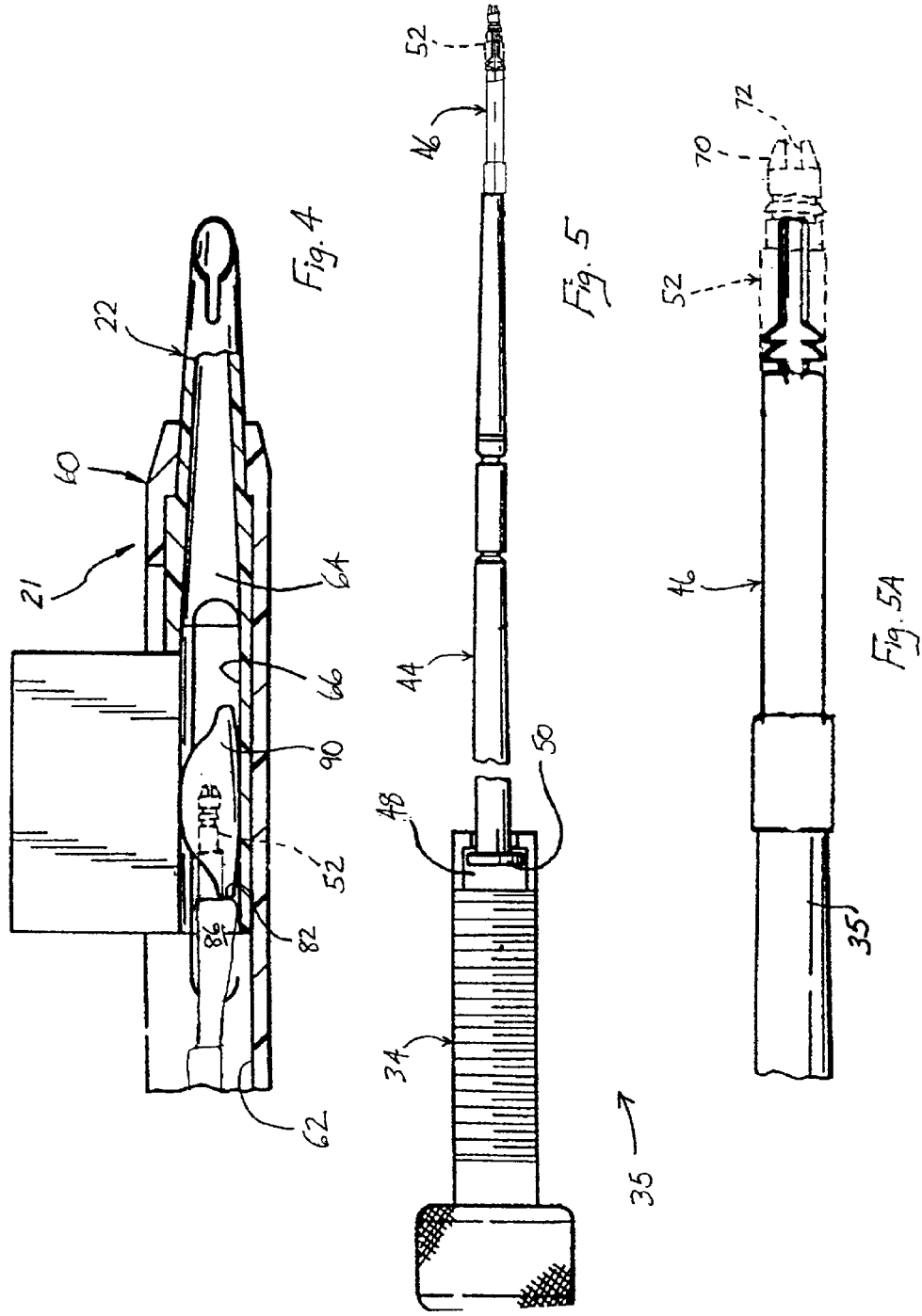

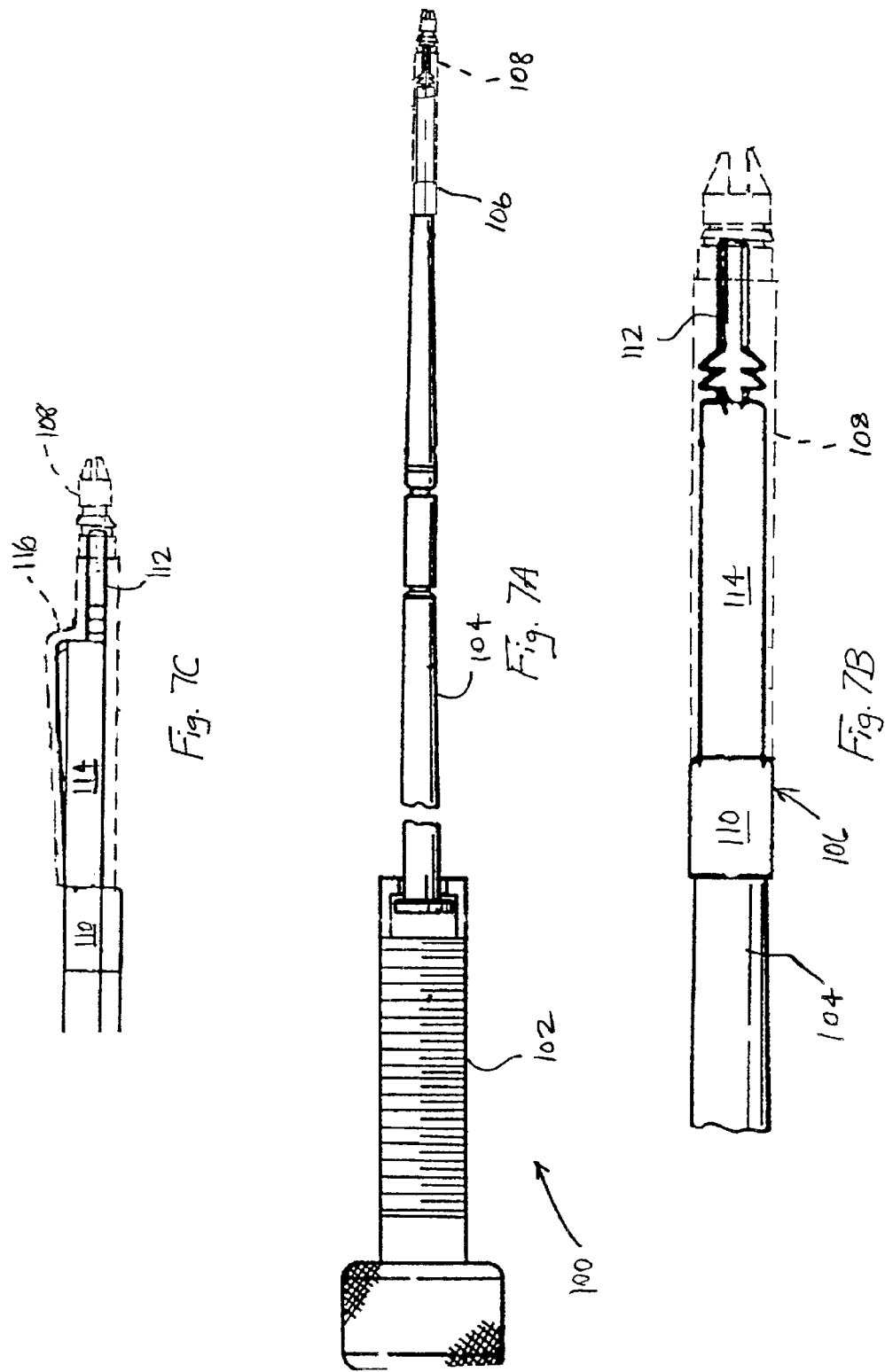

INTRAOCULAR LENS INSERTION APPARATUS

BACKGROUND OF THE INVENTION

The present invention relates to apparatus for inserting an intraocular lens (IOL) into an eye. More particularly, the present invention relates to an insertion apparatus having a hollow tube through which an IOL is pushed with a push rod into an eye in a highly controllable manner.

The human eye is susceptible to numerous disorders and diseases, a number of which attack the crystalline lens. For example, cataracts mar vision through cloudy or opaque discoloration of the lens of the eye. Cataracts often result in partial or complete blindness. If this is the case, the crystalline lens can be removed and replaced with an intraocular lens, or IOL. An IOL may also implanted in the eye to alter the optical properties of (provide vision correction to) an eye in which the natural lens remains.

IOLs often include a disk-like optic, and preferably at least one flexible fixation member or haptic which extends radially outward from the optic and becomes affixed in the eye to secure the lens in position. The optic normally includes an optically clear lens. Implantation of such IOLs into the eye involves making an incision in the eye. It is advantageous, to reduce trauma and speed healing, to have an incision size as small as possible.

The optics may be constructed of deformable biocompatible materials such as silicone polymeric materials, acrylic polymeric materials, hydrogel polymeric materials, and the like. The deformable materials allow the IOL to be rolled or folded for insertion through a small incision into the eye. A substantial number of instruments have been proposed to aid in inserting such a foldable lens in the eye. In a popular apparatus, the optic begins in the shape of a taco and is pushed through a gradually narrowing lumen of an insertion cartridge, progressively rolling into a tubular shape to fit through the incision. Such an exemplary insertion system is disclosed in Makker et al., U.S. Pat. No. 5,942,277, the contents of which are expressly incorporated by reference herein.

In the folding IOL insertion devices such as disclosed by Makker, et al., the cartridge is a disposable polymeric item that is held within a bore of a larger handpiece. A plunger rod associated with and arranged to travel through the handpiece bore has a distal end that lines up with a proximal end of the cartridge lumen and thus can be advanced therethrough. The distal tip contacts and urges the IOL through the cartridge lumen. Various plunger rod tips are known, some pushing on the proximal edge of the IOL optic and some lodging within the taco fold of the optic and "carrying" by outward compression the IOL through the cartridge. In the latter type, such as disclosed in Vidal et al., U.S. Pat. No. 5,776,138, issued Jul. 7, 1998, a soft cover or tip is provided on the plunger rod distal tip to avoid excessive damage of the deformable optic. The soft tip extends a small distance into the optic fold and at a certain linear travel becomes "trapped" therein by compression. This "trapping" of the soft tip within the optic helps control the rate of IOL insertion, and permits rotation of the IOL by the surgeon just as the IOL is released from the cartridge into the eye. The extent of trapping is related to the force required to push the IOL through the tube and the diopter power of the IOL, which alters the thickness of the optic. Therefore, the extent of trapping varies. Unfortunately, excessive trapping can tear the optic and even crack the cartridge tube.

In view of the foregoing, it would be beneficial in the art to provide an IOL insertion apparatus having a soft tip for controlling the IOL insertion rate and permitting IOL rotation which also prevents problems associated with excess trapping of the soft tip in the IOL.

SUMMARY OF THE INVENTION

New, and preferably enhanced, systems for inserting IOLs into eyes have been discovered. The present systems are straightforward and relatively easy to manufacture and use. In addition, such systems advantageously are effective in controlling IOL insertion rate and providing for IOL rotation to reduce, or even substantially eliminate, the risks of one or more problems of the prior art systems, as noted above.

In accordance with the present invention, insertion systems for inserting an IOL having an optic and at least one fixation member into a patient's eye are provided. The systems are of the type that have a handpiece in which is held an insertion cartridge having a proximal loading chamber sized to receive the IOL in a deformed or folded configuration. The loading chamber has an open proximal end. The systems comprise a plunger rod arranged to travel through the handpiece such that a distal tip member of the plunger rod lines up with the open proximal end of the loading chamber and thus can be advanced therethrough and push the IOL through the loading chamber. The plunger rod defines a longitudinal axis and the distal tip member has a longitudinally extending portion that is sized to project and become trapped within the folded intraocular lens and a pusher surface located proximal, preferably just slightly proximal or substantially directly proximal, to and sized larger than the longitudinally extending portion that contacts and pushes the folded intraocular lens optic.

The pusher surface of the plunger rod distal tip member may be offset from the longitudinal axis and define a proximal end of the longitudinally extending portion. The plunger rod distal tip member may be made of a first material, and wherein a soft tip made of a second material softer than a first material covers the longitudinally extending portion and is sized to project and become trapped within the folded intraocular lens. In one embodiment, the pusher surface is formed by a distal face of an elongated mid-portion of the distal tip member. Alternatively, the soft tip also covers the elongated mid-portion and thus covers its distal face such that the pusher surface is formed by the soft tip as it conforms to the distal face. Preferably, the soft tip is made of silicone and includes a slot on its distal end. The elongated mid-portion may have a maximum dimension transverse to the longitudinal axis at its distal face. Furthermore, the distal face may be offset asymmetrically with respect to the longitudinal axis. Desirably, the maximum cross-sectional dimension of the pusher surface is more than about 105% larger than the maximum cross-sectional dimension of the longitudinally extending portion.

In another aspect of the present invention, insertion systems for inserting an IOL having an optic and at least one fixation member into a patient's eye are provided. The systems are of the type that have an insertion cartridge having a proximal loading chamber sized to receive the IOL in a deformed or folded configuration, loading chamber having an open proximal end. The systems include a plunger rod having a distal tip member that fits into the proximal end of the loading chamber and thus can be advanced therethrough and push the IOL through the loading chamber. The plunger rod defines a longitudinal axis and the distal tip member has a control portion that is sized to project and become trapped within the folded IOL. The distal tip member further includes a pusher portion located proximal, preferably just slightly proximal or substantially directly proximal, to and sized larger than the control portion that contacts the folded intraocular lens optic and limits projection of the control portion therewithin.

The pusher portion of the plunger rod distal tip member may be offset from the longitudinal axis and define the proximal end of the control portion. The distal tip member further may be made of a first material, wherein a soft tip made a second material softer than a first material covers the control portion and is sized to project and become trapped within the folded IOLs. In one embodiment, the pusher portion is formed by a distal face of an elongated mid-portion of the distal tip member. In an alternative embodiment, the soft tip also covers the elongated mid-portion and thus covers its distal face such that the pusher portion is formed by the soft tip as it conforms to the distal face. Desirably, the maximum cross-sectional dimension of the pusher portion is more than about 105% larger than the maximum cross-sectional dimension of the control portion.

A further aspect the present invention is directed to methods of urging an IOL having an optic through an insertion cartridge into the eye of a patient. The cartridge has a loading chamber that receives the IOL with the optic in a deformed or folded configuration. The methods include providing a plunger rod having a distal tip member with a longitudinally extending portion and a pusher surface defining the proximal end of the longitudinally extending portion. The distal tip member is advanced into the cartridge such that the longitudinally extending portion projects and becomes trapped within the folded IOLs. The pusher surface contacts the folded intraocular lens optic and limits projection of the longitudinally extending portion therewithin. Further advancing the plunger rod urges the IOL through the cartridge into the eye of the patient.

The longitudinally extending portion becomes trapped within the folded IOL so as to enable the direction of movement of the IOL to be reversed by pulling the distal tip member in a proximal direction. The method therefore further includes slowing the rate of advancement of the IOL through the cartridge by slowing the movement of the plunger rod. A soft tip may cover the longitudinally extending portion of the distal tip member, wherein advancing the distal tip member also advances the soft tip so that it becomes trapped within the folded IOLs.

Each and every feature described herein, and each and every combination of two or more of such features, is included within the scope of the present invention provided that the features included in such a combination are not mutually inconsistent.

Additional aspects, features, and advantages of the present invention are set forth in the following description and claims, particularly when considered in conjunction with the accompanying drawings in which like parts bear like reference numbers.

BRIEF DESCRIPTION OF THE DRAWINGS

FIG. 1 is a perspective view of an IOL insertion system of the present invention showing a handpiece in which a plunger rod travels and an insertion cartridge held at a distal end.

FIG. 2 is a perspective view of the insertion cartridge shown isolated from the system of FIG. 1 and in an open position during an operation in which an IOL is placed in a load chamber.

FIG. 3 is a perspective view of the system of FIG. 1 during an IOL insertion operation.

FIG. 4 is a longitudinal sectional view of the insertion cartridge held closed in the distal end of the handpiece with an IOL therein and showing a distal tip of the plunger rod in the process of urging the lens through the load chamber.

FIG. 5 is a plan view of the plunger rod isolated from the system of FIG. 1 and having a soft tip shown in phantom on a distal end.

FIG. 5A is an enlarged plan view of the distal end of the plunger tip of FIG. 5.

FIG. 7A is a plan view of an alternative plunger rod of the present invention having a soft tip shown in phantom on a distal end.

FIG. 7B is an enlarged plan view of the distal end of the plunger tip of FIG. 7A.

FIG. 7C is an enlarged elevational view of the distal end of the plunger tip of FIG. 7A.

DESCRIPTION OF THE PREFERRED EMBODIMENTS

Figure 6A:
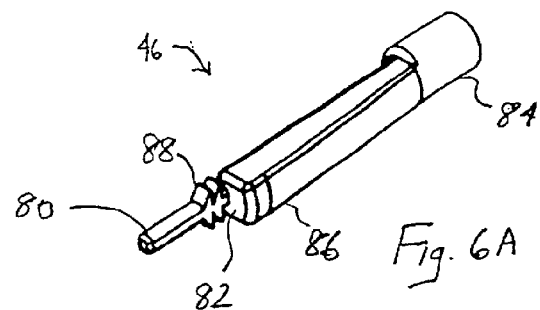
FIG. 6A is a perspective view of an elongate member forming the distal end of the plunger tip of FIG. 5.
Figure 6B:
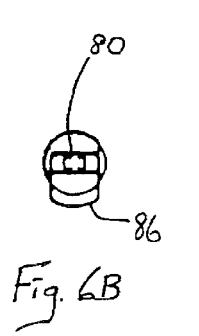
FIGS. 6B and 6C are end and enlarged plan views, respectively, of the distal tip of the elongate member of FIG. 6A.

FIG. 1 illustrates an intraocular lens (IOL) insertion system, shown generally as 20. The system 20 comprises handpiece 21, and a loading cartridge 22 including a forward tube 24 having an open port 26 at its distal end. The handpiece 21 of injection system 20 is an integrally formed unit. Loading cartridge 22 has folding leaves 28a, 28b which extend through an opening 30 in the outer wall of the handpiece 21.

A proximal end portion 32 of handpiece 21 can be sized to completely and closely encompass plunger 34 of a plunger rod assembly 35 (FIG. 5), which has a plunger cap 36 affixed to its proximal end. Proximal end portion 32 is hollow and includes a threaded surface 38, the threads of which matingly engage threads 40 on the outer surface of plunger 34.

Still with reference to FIG. 1, insertion system 20 includes a slot 42 which extends from the proximal portion of opening 30 and connects therewith. Slot 42 is elongated in a direction parallel to the longitudinal axis of insertion system 20. Slot 42 is sufficiently wide to permit the closed folding leaves 28a, 28b to fit therethrough, and sufficiently long to permit loading cartridge 22 to be inserted therein, so that the loading cartridge can be subsequently moved into connecting opening 30. At the same time, the slot 42 is sized to hold the folding leaves 28a, 28b by friction in their fully closed position.

FIG. 5 shows injector plunger rod assembly 35 isolated and having the plunger 34 connected in series to an intermediate elongated rod 44 and a distal tip member 46. The plunger 34 has a locking enclosure 48 on its distal end that holds, without restricting rotation of, an injector rod cap 50 on the proximal end of the elongated rod 44. A soft distal tip 52 is disposed on and may be considered a part of the distal tip member 46.

Distal tip 52 is desirably made of an elastomeric silicone polymer composition which is softer and more elastic than elongated rod 44, which is typically made of titanium. Distal tip 52 is also softer and more elastic than distal tip member 46, which is typically made of a polymeric material, such as reinforced polyamide, liquid crystal polymer and the like. For example, tip 52 is made of a material having a Shore A Hardness value in the range of about 40 to about 80 or about 90 or higher, more specifically about 70 to about 75. Viewed from a different perspective, the tip 52 preferably has a Shore A Hardness value within about 30 of the Shore A Hardness value of the material for which the optic of the IOL to be inserted is made.

As shown in FIG. 4, the distal end portion 60 of handpiece 21 is hollow. When cartridge 22 is inserted into handpiece 21, the hollow space defined by an inner wall 62 of the handpiece 21 is aligned with a hollow space 64 defined by an inner wall 66 of the loading cartridge 22. The combination of the joined handpiece 21 and cartridge 22 can be considered a tubular member defining a hollow space through which the distal tip member 46 and a portion of the connected elongated rod 44 can pass longitudinally.

Distal tip 52 desirably has a length in the range of about 2–50 mm, preferably about 5–25 mm, and more preferably about 10 mm. The length of tip 52 beyond the distal end of distal tip member 46 is in the range of about 0.25–1.0 mm, for example, about 0.75 mm. Tip 52 is generally tapered in the distal direction, with a proximal dimension larger than any other region of the tip. In addition, a distalmost end of the tip 52 is preferably configured to facilitate holding or trapping of at least a portion of the tip of the IOL. Further details of the distalmost end of the tip 52 can be found in Vidal et al., U.S. Pat. No. 5,776,138, the disclosure of which is hereby expressly incorporated by reference.

Distal tip member 46 is sized and adapted to be manually connected to the elongated rod 44. In this context, the distal tip member 46 preferably has sufficient length so as to be conveniently held in the hand of a human as it is being coupled to the rod 44. Particularly useful is a tip member 46 having a length in the range of about 0.5–10.0 cm, more preferably in the range of about 1–5 cm.

The combination of soft distal tip 52 and distal tip member 46 is preferably disposable after a single use, that is after being used to insert a single IOL into an eye. The other components of the IOL insertion system 20, except for loading cartridge 22, are constructed, for example, of metal, so as to be reusable after sterilization.

The distal tip 52 and distal tip member 46 combination can be made in any suitable manner, provided that the tip 52 is secured to the distal tip member 46 and that both components and the combination function as described herein. In one particularly useful embodiment, the distal tip member 46 is molded, for example, using conventional techniques, into the desired form and size. Subsequently, the distal tip 52 is secured to the distal tip member 46, for example, using conventional insert molding techniques.

As seen in FIG. 5A, the distalmost end of tip 52 includes a slotted truncated cone structure 70. A cross slot 72 is formed in the truncated cone structure 70. This feature facilitates introducing the tip 52 into a fold of an IOL as the elongated member and tip combination is moved distally in the hollow space of a tube, as is described hereinafter. However, it should be noted that this slot structure 72 and the truncated cone structure 70 are not necessary in order to achieve substantial benefits in accordance with the present invention.

Distal tip member 46 may be coupled to rod 44 in any suitable manner. The coupling between the distal tip member 46 and the rod 44 should be sufficiently strong or secure so that these two components remain joined as the IOL insertion system 20 is used to insert an IOL into an eye.

Figure 5B:
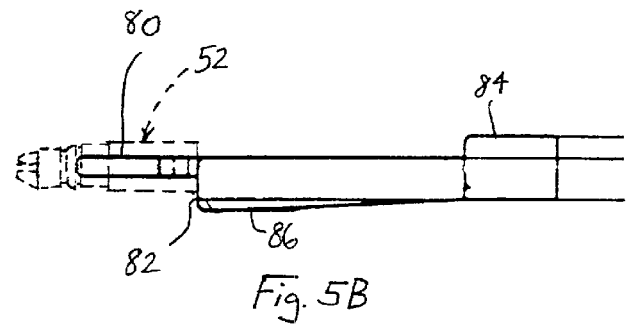
FIG. 5B is an enlarged elevational view of the distal end of the plunger tip of FIG. 5.
Figure 6C:
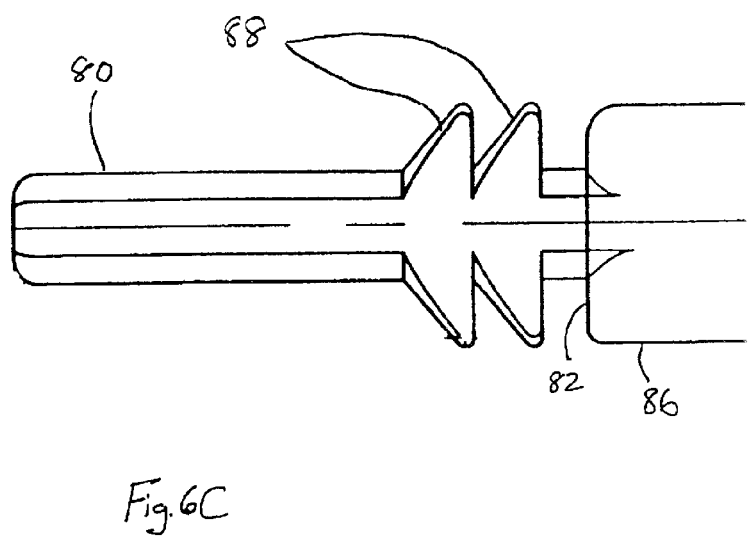

Distal tip member 46 is shown in greater detail in FIGS. 5B and 6A–6C and includes a distal extension 80 that begins at a pusher surface 82. That is, the pusher surface 82 forms the proximal end of the distal extension 80. A proximal coupling 84 is adapted to mate with the distal end of the elongated rod 44. The pusher surface 82 comprises the distal face of an enlarged mid-portion 86 that extends between the distal extension 80 and the proximal coupling 84. The radial cross-section of the pusher surface 82 is larger than the rest of the mid-portion 86. That is, as best seen in FIG. 5B, the mid-portion 86 gradually narrows in a proximal direction. The pusher surface 82 has a larger radial dimension than the distal extension 80, which is a configuration that improves control of advancement of the IOL, as will be described below. As also see in FIG. 6B, the mid-portion 86 is laterally offset from a centerline of the tip member 46, which centerline extends though the center of the distal extension 80.

The distal extension 80 has a generally rounded rectangular parallelpiped shape except for two pairs of oppositely directed triangular grippers 88. The gripper 88 help retain the soft distal tip 52 on the tip member 46. That is, whether the tip 52 is molded over the tip member 46 or simply slipped over, the grippers 88 provide a greater frictional resistance to separation thereof.

FIGS. 4 and 5A–5B illustrate a relatively short distal tip 52 that covers just the distal extension 80 and extends slightly beyond. As mentioned above, the truncated cone structure 70 at the distalmost end of tip 52 extends between about 0.25–1.0 mm beyond the distal extension 80. The proximal end of the tip 52 abuts the pusher surface 82. As seen in FIG. 4, therefore, the soft distal tip 52 extends within the fold of an IOL 90, and the pusher surface 82 may contact and push on a proximal edge of the IOL 90. In this way, the pusher surface 82 not only provides a positive pushing surface to urge the IOL 90 through the cartridge bore defined by the inner wall 66 thereof, but also limits the extent to which the soft distal tip 52 extends within the IOL 90. This latter feature prevents excessive trapping and the potential for consequential damage to the IOL 90.

The distal tip 52 becomes trapped within the folded IOL 90 so as to enable the direction of movement of the IOL 90 to be reversed by pulling the distal tip member 46 in a proximal direction. Consequently, the surgeon can pull the IOL 90 back or just slow the rate of advancement of the IOL 90 through the cartridge by slowing the movement of the plunger rod.

Although positive engagement of the proximal edge of the IOL 90 by the pusher surface 82 is possible, the nature of the soft and lubricated material of the IOL may hinder such direct contact. However, the radial dimension (e.g., diameter)of the pusher surface 82 is such that it will not travel too far into the fold of the IOL 90 before such relative movement stops. That is, the pusher surface 82 very quickly fills the fold of the IOL 90 and compresses it against the inner lumen of the cartridge 22. Further movement of the pusher surface 82 pushes IOL 90 along the cartridge lumen. To ensure such an interaction, the cross-sectional dimensions of the cartridge lumen, pusher surface 82, and IOL 90 must be coordinated. Furthermore, the relative cross-sectional dimensions of the distal extension 80 and pusher surface 82 are such that the distal extension passes into the fold of the IOL 90 and assumes a frictional contact therewith, yet the pusher surface will not enter the fold or will only enter a short distance before becoming trapped.

In one embodiment, the cartridge lumen is cylindrical and has a particular maximum diameter, for example 1.9 mm. One way to quantify the pusher surface 82 size is relative to the cartridge lumen. The maximum cross-sectional dimension of the pusher surface 82 is desirably about 75% or more of the diameter of the cartridge lumen, preferably more than about 90%. Alternatively, the maximum cross-sectional dimension of the pusher surface 82 is desirably about 105% or more of the maximum cross-sectional dimension of the distal extension 80, preferably more than about 120%.

FIGS. 7A–7C illustrate an alternative embodiment of a plunger rod assembly 100 of the present invention. The assembly includes a plunger 102, an elongated rod 104, a distal tip member 106, and a soft distal tip 108. The first three components are as described above, and thus will not be further examined. The soft distal tip 108 is longer than the tp 52 described above, and extends from just slightly beyond the distalmost end of distal tip member 106 to a proximal coupling 110 of the tip member. In other words, the tip 108 covers both a distal extension 112 and an enlarged midportion 114.

The soft tip 108 is of a material that closely conforms to the contours of the distal tip member 106, as best seen in FIG. 7C. More specifically, the tip 108 expands outward at the beginning of the enlarged mid-portion 114 to form a pusher surface 116. The combined distal tip member 106 and soft tip 108 function in a manner similar to the first embodiment described above to urge an IOL though an insertion cartridge. In particular, the soft tip 108 extends into and is trapped within the folded IOL, and the pusher surface 116 may contact a proximal edge of the IOL, or at least will not pass far into the fold of the IOL before becoming trapped. In this way, great control over the advancement of the IOL is provided by the trapped soft tip 108, but excess trapping is avoided. Furthermore, contact of the pusher surface 116 with the proximal edge of the IOL, or initial inner wall, provides a soft, non-damaging positive pushing force. At the same time, the trapped soft tip 108 enables the surgeon to reverse the direction of the IOL advancement if necessary.

FIG. 2 illustrates the manner in which loading cartridge 22 facilitates folding an IOL 90. The hinged folding leaves 28a, 28b are used to open and close folding tubular halves 120 and 122, respectively. IOL 90 (in an unfolded state) is placed on folding tubular halves 120 and 122, by forceps 124. The forceps 124 hold the IOL 90 in a specific and determinable planar orientation. Superior fixation member or haptic 126 is placed forward of optic 128, while the other haptic 130 trails the optic. Hinged folding leaves 28a, 28b are moved together, which folds the flexible or foldable optic 128 of IOL 90 in half. After IOL 90 is folded, the forceps 124 is removed.

The closed loading cartridge 22, containing the folded IOL 90, is then loaded into handpiece 21 of insertion system 20, as described above. An effective amount of a lubricant composition, such as a visco-elastic material, for example, a conventional sodium hyaluronate-containing aqueous material, preferably is included in the hollow space defined by the loading cartridge 22. This lubricant composition allows the folded IOL 90 to more easily pass through the hollow space defined by loading cartridge 22.

Insertion system 20 is operated and functions as follows. When it is desired to insert IOL 90 into an eye, the system 20 is placed in a configuration as shown in FIG. 1, with distal tip member 46 (with tip 52) secured to rod 44, as shown in FIG. 5.

With the IOL 90 in its folded condition within system 20, the operator (surgeon) advances plunger 34 distally by rotating cap 36. This action advances rod 44 and distal tip member 46 distally. As rod 44 and distal tip member 46 are moved distally, the tip 52 comes into contact with folded optic 128 and is introduced into the fold of the folded optic as shown in FIG. 4. Because of the relative softness and elasticity of tip 52, the distal movement of rod 44 and distal tip member 46 causes the tip to become trapped in the fold of the folded optic 128. The folded optic 128 can be considered to be controlled, pulled or carried by the rod 44, distal tip member 46 and tip 52 when the tip is trapped in the fold.

Referring now to FIG. 3, the IOL 90 is to be placed in eye 140 into an area formerly occupied by the natural lens of the eye. With the IOL 90 in its folded position within system 20, and tip 52 trapped in the fold of the folded optic 128, forward tube 24 is ready for insertion through an incision in the sclera 142 of eye 140. Capsular bag 144 protects the posterior segment of the eye 140. With the forward tube 24 inserted within the eye 140 and the port 26 positioned so that the IOL 90 can unfold in the location within the eye best suited for permanent implantation, the operator advances plunger 34 by rotating cap 36. This action advances rod 44, distal tip member 46, tip 52 and IOL 90 distally into the forward tube 24.

As rod 44 advances farther distally, the IOL exits the port 26 in a controlled manner and is controllably released in a location as close as possible to the IOL's final implanted position.

FIG. 3 shows the sclera 142 having an incision through which the distal end portion of forward tube 24 is passed. Alternately, the incision can be made through the cornea or other portion of the eye. Forward tube 24 has a sufficiently small cross-section to pass into the eye 140 through a 3.0 mm incision in the sclera 102. Folding leaves 28a, 28b, in contact with each other when lens loading cartridge 22 is in a closed position, can be grasped by an operator and used to guide and position insertion tube 24 in its desired position within the eye.

After IOL 90 has been inserted into eye 140, forward tube 24 is removed from the eye. The tip 52 can be used to position the IOL 90 in the eye. For example, the tip 52 can be retracted (after the optic is released) and then used to push the trailing haptic 130 out of the tube and position this haptic into the eye. If needed, IOL 90 can be repositioned in the eye by a small, bent needle or similar tool inserted into the same incision.

Once IOL 90 is properly positioned in eye 140 and system 20 is withdrawn from the eye, the incision in the sclera may be closed, for example, using conventional techniques. After use, loading cartridge 22 and distal tip member 46 (including tip 52) are preferably disposed of. Remaining portions of system 20, in particular the plunger 34 and rod 44 can be reused after sterilization and disinfection.

Enhanced lubricity resulting from a component incorporated into the material of the cartridge facilitates advancement and folding of the IOL so that a reduced amount of force is required to pass the IOL through the cartridge. Another benefit to this lubricity is that the degree of folding of the IOL may be increased so that ultimately the IOL can be inserted through an even smaller incision.

While the present invention has been described with respect to various specific examples and embodiments, it is to be understood that the invention is not limited thereto and that it can be variously practiced within the scope of the following claims.

What is claimed is:

1. An insertion system for inserting an intraocular lens having an optic and at least one fixation member into a patient's eye, the system being of the type that has a handpiece in which is held an insertion cartridge having a proximal loading chamber sized to receive the intraocular lens in a folded configuration, the loading chamber having an open proximal end, the system comprising:

a plunger rod arranged to travel through the handpiece such that a distal tip member of the plunger rod lines up with the open proximal end of the loading chamber and thus can be advanced there through and push the intraocular lens through the loading chamber, the plunger rod defining a longitudinal axis and the distal tip member having a longitudinally extending portion that is sized to project and become trapped within the folded intraocular lens and a pusher surface locate proximal to and sized larger than the longitudinally extending portion that contacts and pushes the folded intraocular lens optic, wherein the pusher surface of the plunger rod distal tip member is offset from the longitudinal axis, the plunger rod distal tip member being made of a first material; and a soft tip made of a second material softer than the first material covering the longitudinally extending portion and sized to project and become trapped within the folded intraocular lens.

2. The system of claim 1, wherein the pusher surface is formed by a distal face of an elongated mid-portion of the distal tip member.

3. The system of claim 1, wherein the longitudinally extending portion is generally uniform in cross-section transverse to the longitudinal axis except for at least one pair of oppositely directed grippers that extends outward and helps hold the soft tip thereon.

4. The system of claim 1, wherein the distal tip member further includes an elongated mid-portion having a distal face at the beginning of the longitudinally extending portion, and wherein the soft tip also covers the elongated mid-portion and thus covers its distal face such that the pusher surface is formed by the soft tip as it conforms to the distal face.

5. The system of claim 1, wherein the soft tip is made of silicone and included a slot on its distal end.

6. The system of claim 1, wherein the plunger rod comprises a proximal plunger, an intermediate rod, and the distal tip member, and wherein the plunger and rod are each made of he material that can be sterilized, while the distal tip member is disposable.

7. The system of claim 6, wherein the distal tip member includes a proximal coupling adapted to mate with a distal end of the rod and an elongated mid-portion extending between the proximal coupling and the longitudinally extending portion, wherein the pusher surface is formed by distal face of the elongated mid-portion.

8. The system of claim 7, wherein the elongated mid-portion has a maximum dimension transverse to the longitudinal axis at its distal face, and wherein the distal face is offset asymmetrically with respect to the longitudinal axis.

9. An insertion system for inserting an intraocular lens having an optic and at least one fixation member into a patient's eye, the system being of the type that has an insertion cartridge having a proximal loading chamber sized to receive the intraocular lens in a folded configuration, the loading chamber having an open proximal end, the system comprising:

a plunger rod having a distal tip member that fits into the proximal end of the loading chamber and thus can be advanced there through and push the intraocular lens through the loading chamber, the plunger rod defining a control portion that is sized to project and become trapped within the folded intraocular lens and a pusher portion located proximal to and sized larger than the control portion that contacts and pushes the folded intraocular lens optic and limits projection of the control portion there within, wherein the pusher portion of the plunger rod distal tip member is offset from the longitudinal axis, the plunger rod distal tip member being made of a first material; and a soft tip made of a second material softer than the first material covering the control portion and sized to project and become trapped within the folded intraocular lens.

10. The system of claim 9, wherein pusher portion is formed by a distal face of an elongated mid-portion of the distal tip member.

11. The system of claim 9, wherein the control portion is generally uniform in cross-section transverse to the longitudinal axis except for at least one pair of oppositely directed grippers that extends outward and helps hold the soft tip thereon.

12. The system of claim 9, wherein the distal tip member further includes an elongated mid-portion having a distal face at the proximal end of the control portion, and wherein the soft tip also covers the elongated mid-portion and thus covers its distal face such that the pusher portion is formed by the soft as it conforms to the distal face.

13. The system of claim 9, wherein the soft tip is made of silicone and includes a slot on its distal end.

14. The system of claim 9, wherein the plunger rod comprises a proximal plunger, an intermediate rod, and the distal tip member, and wherein the plunger and rod are each made of the material that can be sterilized, while the distal tip member is disposable.

15.The system of claim 14, wherein the distal tip member includes a proximal coupling adapted to mate with a distal end of the rod and an elongated mid-portion extending between the proximal coupling and the control portion, wherein the pusher portion is formed by a distal face of the elongated mid-portion.

16. The system of claim 15, wherein the elongated mid-portion has a maximum dimension transverse to the longitudinal axis at its distal face, and wherein the distal face is offset asymmetrically with respect to the longitudinal axis.

* * * * *

UNITED STATES PATENT AND TRADEMARK OFFICE
CERTIFICATE OF CORRECTION

PATENT NO. : 6,923,815 B2  
DATED : August 2, 2005  
INVENTOR(S) : Daniel D. Brady and Harish C. Makker It is certified that error appears in the above-identified patent and that said Letters Patent is hereby corrected as shown below:

<u>Column 9,</u>  
Line 17, "locate" should be -- located --.  
Line 48, should read as -- made of the material --.  
Line 58, should read as -- a distal face of the elongated mid-portion. --.

<u>Column 10,</u>  
Line 38, should read as -- by the soft tip as it conforms to the distal face. --.

Signed and Sealed this

Eighteenth Day of April, 2006

JON W. DUDAS  
*Director of the United States Patent and Trademark Office*